US011666480B2

(12) United States Patent
Cominato Filho et al.

(10) Patent No.: US 11,666,480 B2
(45) Date of Patent: Jun. 6, 2023

(54) ARRANGEMENT APPLIED TO A CAP FOR COOLING THE SCALP

(71) Applicants: Gianmaria Cominato Filho, Taubaté (BR); Hezio Jadir Fernandes Junior, Taubaté (BR)

(72) Inventors: Gianmaria Cominato Filho, Taubaté (BR); Hezio Jadir Fernandes Junior, Taubaté (BR)

( * ) Notice: Subject to any disclaimer, the term of this patent is extended or adjusted under 35 U.S.C. 154(b) by 434 days.

(21) Appl. No.: 16/638,902

(22) PCT Filed: Jul. 25, 2018

(86) PCT No.: PCT/BR2018/050252
§ 371 (c)(1),
(2) Date: Feb. 13, 2020

(87) PCT Pub. No.: WO2019/033186
PCT Pub. Date: Feb. 21, 2019

(65) Prior Publication Data
US 2020/0360177 A1 Nov. 19, 2020

(30) Foreign Application Priority Data

Aug. 14, 2017 (BR) .......................... 2020170173742

(51) Int. Cl.
*A61F 7/02* (2006.01)
*A61F 7/00* (2006.01)

(52) U.S. Cl.
CPC ........ *A61F 7/02* (2013.01); *A61F 2007/0008* (2013.01); *A61F 2007/0052* (2013.01);
(Continued)

(58) Field of Classification Search
CPC ...... A61F 2007/0063; A61F 2007/0064; A61F 2007/0065; A61F 2007/0067; A61F 2007/0068
See application file for complete search history.

(56) References Cited

U.S. PATENT DOCUMENTS

| 3,273,162 A | * | 9/1966 | Andrews, III | ......... A42B 3/065 |
| | | | | D29/104 |
| 3,908,655 A | * | 9/1975 | Lund | ..................... A61M 19/00 |
| | | | | 604/23 |

(Continued)

FOREIGN PATENT DOCUMENTS

| CN | 107854211 A | 3/2018 |
| DE | 8911157 U1 | 11/1989 |

(Continued)

OTHER PUBLICATIONS

International Search Report & Written Opinions, PCT/BR2018/050252, dated Sep. 18, 2018, 7 pages, Non-English.

(Continued)

*Primary Examiner* — Kaitlyn E Smith
(74) *Attorney, Agent, or Firm* — Goodhue, Coleman & Owens, P.C.

(57) ABSTRACT

Refers to equipment (E), the objective of which is to take extremely cold air to a cap (1) comprised by a cylindrical duct (2), located in the upper part of the cylindrical structure (3) of the cap (1) which is coated by a thermal foam (ESP) and any given material (M), wherein the cylindrical duct (2) overlaps a sprinkler (ASP), which is located in the inner part (I) of the cylindrical structure (3) of the cap (1), further, the cap (1) comprises fins (4) which form an angle of 90° in relation to the inner walls (I) of the cylindrical structure (3) of the cap (1), which finally also has reinforcement ribs (5) and a circular support (6) endowed with a central hollow (7) circular and/or oval coated by a thermal foam (ESP) throughout its perimeter.

19 Claims, 7 Drawing Sheets

(52) U.S. Cl.
CPC ............... *A61F 2007/0212* (2013.01); *A61F 2007/0282* (2013.01); *A61F 2007/0295* (2013.01)

(56) References Cited

U.S. PATENT DOCUMENTS

| | | | |
|---|---|---|---|
| 4,888,958 A | * 12/1989 | Ella | ................ A61F 7/0085 454/238 |
| 5,603,728 A | 2/1997 | Pachys | |
| 6,156,059 A | 12/2000 | Olofsson | |

FOREIGN PATENT DOCUMENTS

| | | | | |
|---|---|---|---|---|
| JP | 6189228 B2 | | 8/2017 | |
| WO | WO8204184 | * | 12/1982 | ............... A61F 7/10 |

OTHER PUBLICATIONS

International Search Report, PCT/BR2018/050252, dated Sep. 18, 2018, 3 pages, English translation.

* cited by examiner

ARRANGEMENT APPLIED TO A CAP FOR COOLING THE SCALP

BRIEF PRESENTATION

The present patent application refers to an ARRANGEMENT APPLIED TO CAP FOR COOLING THE SCALP, which is designed to perform the cooling of the scalp in patients undergoing chemotherapy, by fusing a cap capable of injecting extremely cold turbulent air into the entire scalp region of the patient in question, in order to prevent alopecia (hair loss).

FIELD OF APPLICATION

The field of application of the innovation now claimed is focused on patients undergoing chemotherapy in clinics, hospitals and the like.

PERSUASION

As generally known, there are various models of caps for chemotherapy treatments on the market today. The methods for cooling the scalp have the following forms of use: The first is carried out by contact, with gel caps or circulating liquid caps. The second form is carried out by way of helmet and/or cap that includes external equipment that generates cold air for the helmet and/or cap. The drawback of the cap by contact is because it is unable to cover the patient's head perfectly, this method of cooling may cause partial alopecia (hair loss), that is, the contact cooling method leaves some regions of the patient's head devoid of cooling, which causes partial hair loss after chemotherapy treatment.

The helmet and/or cap that includes external equipment generating cold air as cited above tends to perform the cooling of the scalp at a temperature of 3° C. to 7° C., among other temperatures, which is not sufficient to cool the scalp effectively in order to avoid alopecia (hair loss) in patients undergoing chemotherapy, since the cold air injected by this method is recovered by means of a recirculating circuit, in a laminar flow with low absorption of the cold by the scalp, which inevitably will not cool the scalp evenly and effectively.

Other drawbacks such as, for example, occur due to the weight the cap contains, because in this way, the patient undergoing chemotherapy treatment for a extended time gets very tired, facing muscular pains in the back and neck regions. Another drawback of conventional caps is that they oblige the patient to hold it with his/her own or a supporting arm, which certainly causes discomfort and pains in the arm, further, it limits the patient, as he/she cannot move his/her head, is unable to get up, thus making one remain static for a long time.

CURRENT STATE OF THE ART

The current state of the art anticipates some patent documents which refer to the subject matter at hand, such as document WO1989009583A2, wherein the scalp cooling system is described such that a current is recirculated to reduce the existing moisture, initially to the air circuit and for the direct contribution of moisture resulting from evaporation from the scalp, and by combining the impedance between the delivery tube and evaporation orifice to heat the air received and cool the air extracted. In its structure, an application cap has an air delivery gallery which directs the air to the scalp and to the hairline through a number of perforations, in the profile of the same size and profile to minimize the losses of friction in the air current. The air is extracted at the top of the cap where the convergence and the increasing speed of the air compensates the increased temperature of the air, such that at this moment, the cooling of the scalp is optimized by using the cooling rate effect. The interior of the cap includes a number of spacers which are kept in subtle contact with the scalp by applying a slight force on the cap using a counterbalanced arm. This enables the cap to stay in contact with the scalp even if the patient relaxes and falls from the chair during treatment. The cap is also supplied with a skirt made of elastic fabric to reduce the loss of the closed air recirculation circuit.

The document above describes an apparatus for cooling the scalp using cold air by closed circuit system, where a cap or helmet is applied to the patient and cold air is injected through an air input connection in this cap/helmet and by way of another connection, the output, the hot air from the body heat is withdrawn from the scalp. This withdrawn air goes to the equipment which again cools this air and re-injects it into the cap/helmet. The working temperature of this cold air equipment is from 3° C. to 7° C.; additionally, the cap due to the weight must be supported by an arm that supports it, causing tiredness for the patient, further, the cap mentioned in the cited patent has a double layer and various holes through which the injected air is dispersed to come into contact with the scalp and afterwards this air is withdrawn by the upper orifice to return to the equipment.

The document US20140046410A1 refers to a system and method for cooling the scalp in order to prevent hair loss in patients undergoing chemotherapy is a cooled cap, a recirculation using the cold water system of circulatory hoses, a reservoir, a circulatory pump and a powerful supply, and the method has the steps to provide a cooled cap with the recirculation of the cold water system for cooling the cooled cap; positioning the cooled cap on the patient's head for at least 30 minutes before he/she undergoes chemotherapy; during chemotherapy; and keeping the cooled cap on the patient's head for at least 90 minutes after chemotherapy with the recirculation of cold water system moved by a conventional supply of an electric power or by an electric power from a vehicle with a 12 Volt connection such as a lighter according to the possible need.

The document above basically describes a cap with recirculation water system, which does not even generate cooling of the patient's scalp, so it causes hair loss to the patient during chemotherapy treatment.

OBJECTIVES OF THE INNOVATION

It is an objective of the present innovation to provide patients undergoing chemotherapy a cap capable of injecting extremely cold turbulent air throughout the scalp region thereof evenly in order to prevent alopecia (hair loss);

It is an objective of the present innovation to prevent the accumulation of hot air coming from the patient's scalp inside the cap, as it is capable of distributing extremely cold turbulent air throughout the patient's scalp region, while said extremely cold turbulent air leaves in a continuous flow through the lower edge of the cap, which overlaps the patient's head, and does not return thereto;

It is an objective of the present innovation to propose a cap comprising an easy-fit and light structure such that there is no need to extend the arm to support the cap since it stays perfectly encased on the head, and because it is coated by a thermal foam that makes it light and cozy;

Lastly, it is an objective of the present innovation to propose a cap the enables full mobility of the patient, wherein he/she may have freedom of locomotion in order to get comfortable freely on his/her bed, and even get up to wrap up and or remove said clothing, among others.

INNOVATION

In acknowledgement of the state of the art, its gaps and limitations, the inventor, after studies and research created an ARRANGEMENT APPLIED TO CAP FOR COOLING THE SCALP, which basically consists of a cylindrical duct located in the upper part of the cap, which comprises a cylindrical structure, which internally presents a sprinkler just below the cylindrical duct, whereas the cold air generated by equipment that is part of the present innovation, runs through the hose in a laminar jet until it arrives at said cylindrical duct, and next the air is injected into the sprinkler, which directs the cold air to the entire inner perimeter of the cap, that is, through the entire inner wall of the cap, and said air passes through fins included in the inner walls thereof, which form an angle of 90° in relation to the wall and the upper part of the cap. Therefore, the cold air directed to the entire inner perimeter of the cap, reaches the fins cited above, and ribs which are located in the lower inner part of the cap, passes through a circular support which is endowed with a central hollow equally circular and coated by thermal foam, transforming the cold air injected therein into a turbulent and continuous flow such that it is dispersed onto patient's scalp, reaching the entire scalp region thereof. The objective of the circular support endowed with a central hollow is to fit onto the patient's head in a cozy manner.

Therefore, the cap is to shape a light and easy-fit cap so that the patient does not need to anchor the cap with his/her arm, and is designed to offer convenience, practicality and comfort for the patient. Furthermore, it is designed to inject extremely cold turbulent air onto the entire scalp region of the patient in question, in order to prevent alopecia (hair loss).

DESCRIPTION OF THE DRAWINGS

The accompanying drawings, as listed below, are for an improved understanding.

DETAILED TECHNICAL DESCRIPTION OF THE INNOVATION

Figure 1:
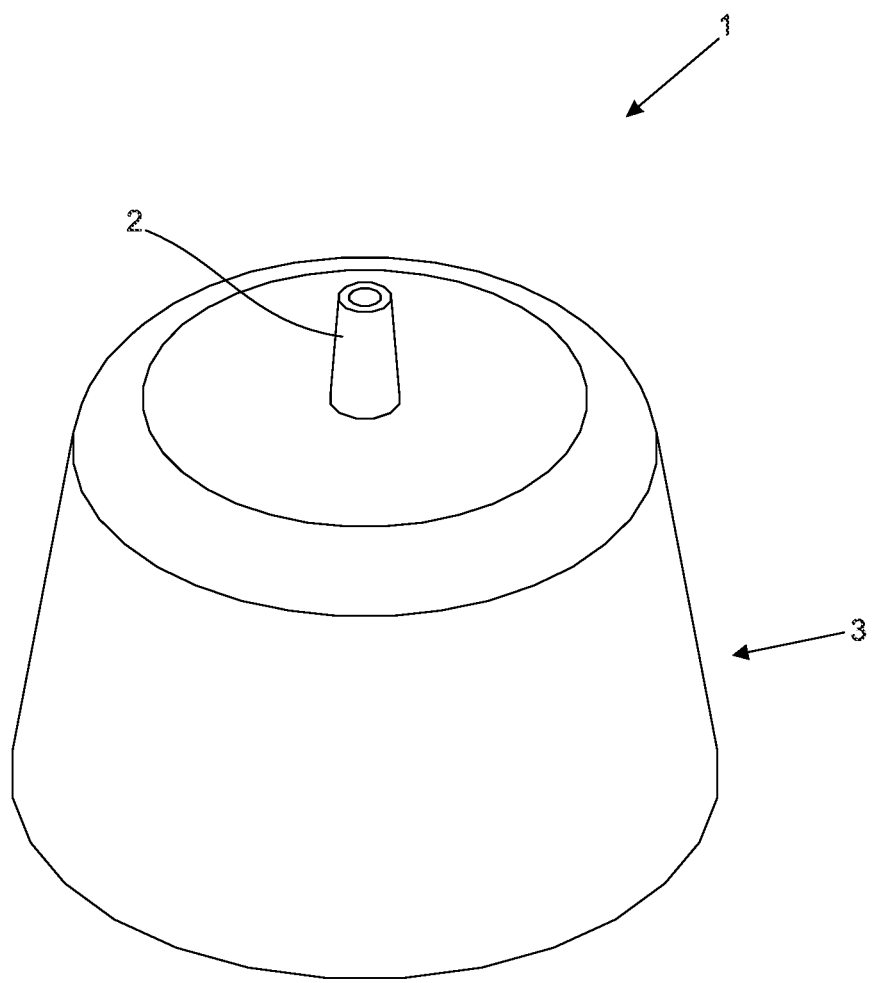
FIG. 1: Perspective view of the arrangement applied to cap for cooling the scalp.

The ARRANGEMENT APPLIED TO CAP FOR COOLING THE SCALP, the object of this patent application, refers to an item equipment (E), the objective of which is to take extremely cold air to a cap (1) comprised by a cylindrical duct (2), located in the upper part of the cylindrical structure of the cap (1), which is coated by a thermal foam (ESP) and any material (M), wherein the cylindrical duct (2) overlaps a sprinkler (ASP), which is located in the inner part (I) of the cylindrical structure (3) of the cap (1), which further, the cap (1) comprises fins (4) which form an angle of 90° in relation to the inner walls (I) of the cylindrical structure (3) of the cap (1), which lastly also presents reinforcement ribs (5) and a circular support (6) endowed with a central hollow (7) circular and/or oval, coated by a thermal foam (ESP) throughout its perimeter.

More particularly, the cooling equipment (E) comprises a cooling compressor, which forwards the compressed air to a condenser where it exchanges heat with the environment, turning into liquid state. At the end of the condenser, the liquid passes through an expansion valve which reduces its pressure, entering the evaporator serpentine, already in the cold phase, this serpentine being directed to a cold chamber, bearing in mind it houses the aforementioned serpentine. Therefore, the air captured in the environment is thrown by compressor, at high pressure, inwardly of said cold chamber, where the temperature is reduced to a range of −20 to −35° C., endowed with top opening from where it derives to a hose (8), endowed with a connector (9) at its end, which connects to a cylindrical duct (2) located in the upper part of the cap (1), which comprises a cylindrical structure (3), which internally (I) presents a sprinkler (ASP) just below the cylindrical duct (2), while the cold air generated by the equipment (E), runs through the hose (8), in a laminar jet until it reaches said sprinkler (ASP), which directs the cold air, to the entire inner perimeter (I) of the cap (1) which is endowed with fins (4) which form an angle of 90° in relation to the inner wall (I) of the cap (1). The cold air directed to the entire inner perimeter (I) of the cap (1), reaches the fins (4) cited above, and reinforcement ribs (5) that are located in the lower inner part (I) of the cap (1), transforming the extremely cold air into a turbulent and continuous flow, such that the air is distributed evenly, causing the heat from the scalp to be dispersed, wherein the extremely cold turbulent air reaches the patient's entire scalp region, at an ideal temperature, in order to prevent alopecia which is no more than the patient's hair loss. Even so, the cap (1) by means of a circular support (6) endowed with a central hollow (7) equally circular and/or oval, allows the patient to perform such fitting between his/her head and the cap (1) in a practical and comfortable manner; lastly, the cap (1) is coated by a thermal foam (ESP) and any type of material (M) which coats the thermal foam (ESP). The circular support (6) endowed with a central hollow (7) circular and/or oval is also coated by a thermal foam (ESP) throughout its perimeter, in order to provide the patient comfortable and cozy treatment.

Therefore, the present innovation is to shape a cap (1) having a light structure and easy to fit onto the patient's head, wherein it does not need to anchor the cap (1) with the arm, as seen in the current state of the art, and is also designed to offer convenience, practicality and comfort to the patient. Furthermore, it is designed to inject extremely cold turbulent air into the patient's entire scalp region evenly and at the ideal temperature, in order to prevent alopecia (hair loss).

Figure 2:
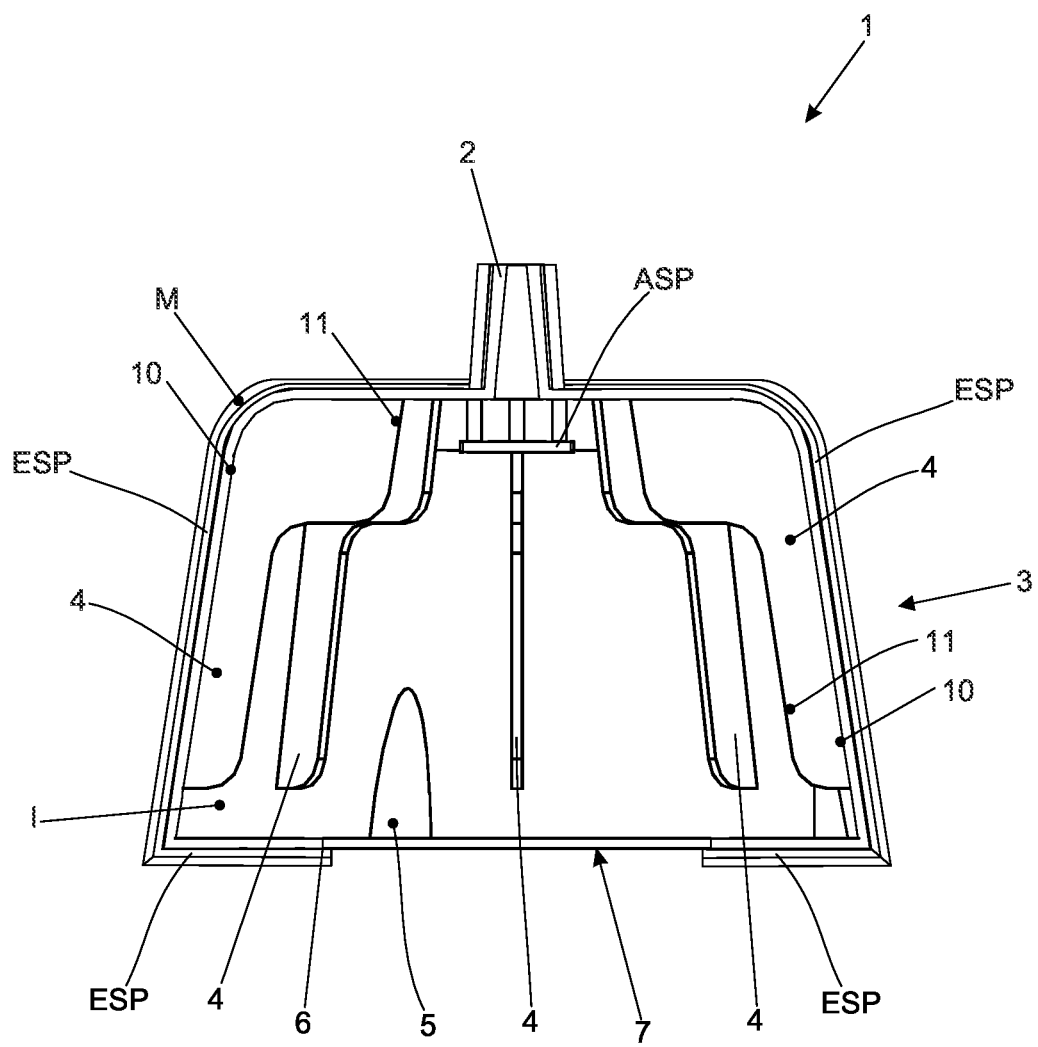
FIG. 2: Cutaway view of the arrangement applied to cap for cooling the scalp.
Figure 3:
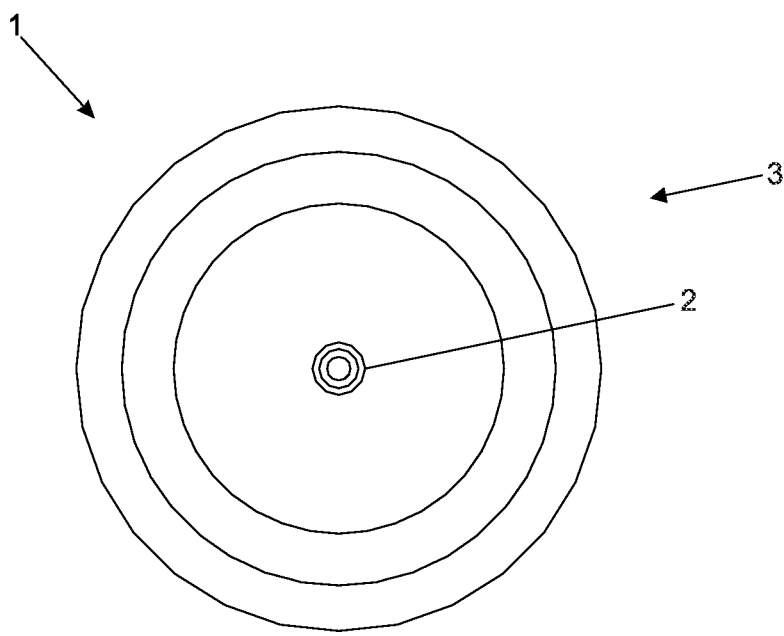
FIG. 3: Top view of the arrangement applied to cap for cooling the scalp.
Figure 4:
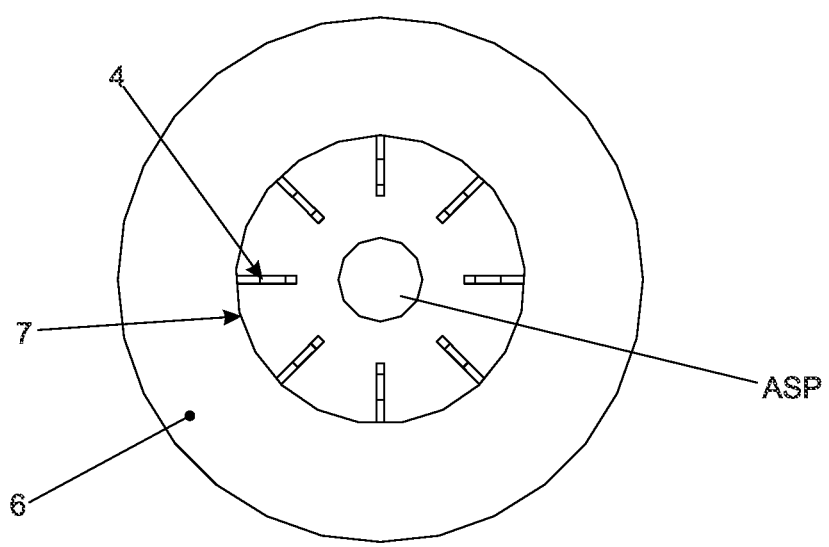
FIG. 4: Bottom view of the arrangement applied to cap for cooling the scalp.
Figure 5:
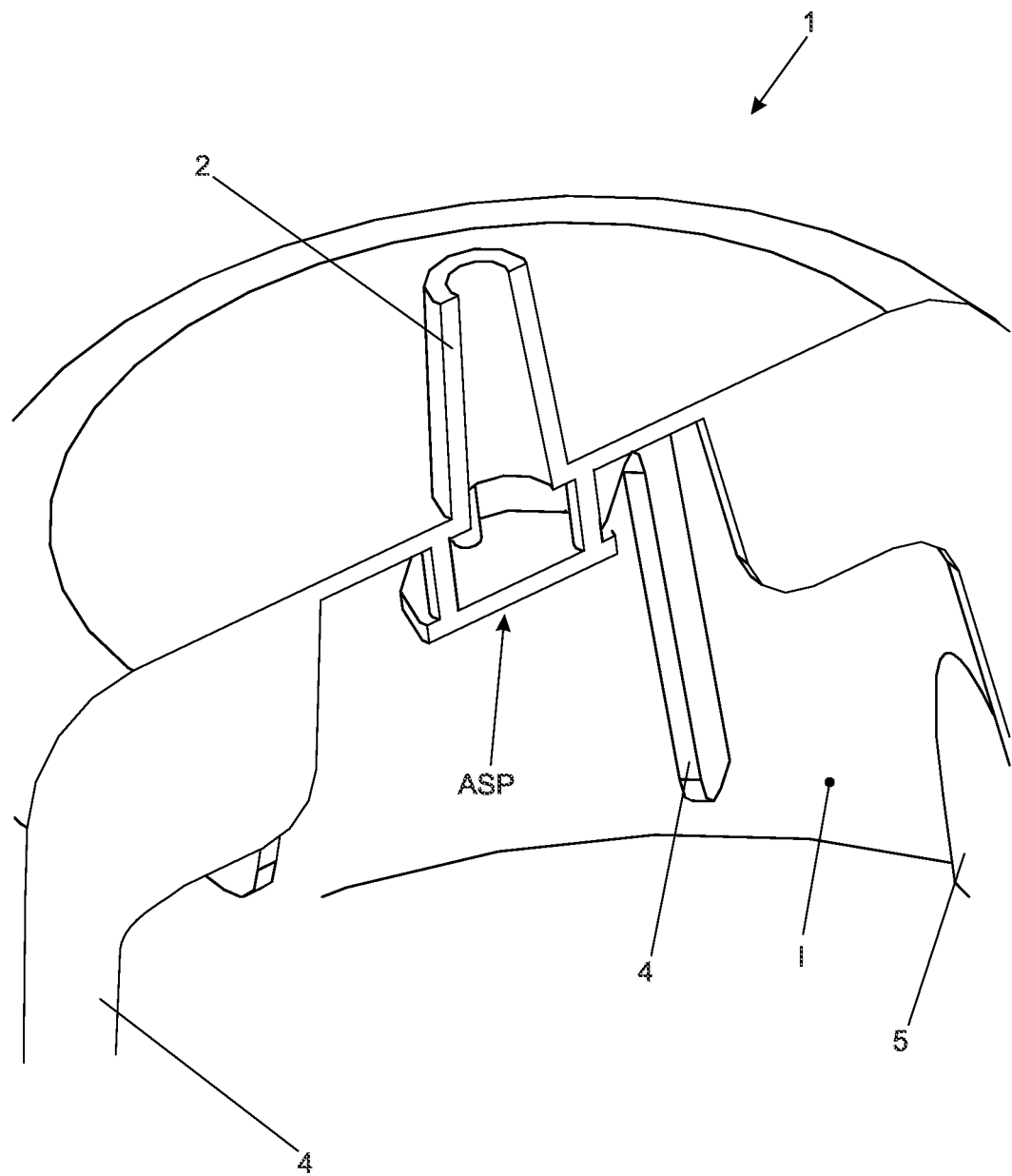
FIG. 5: Partial cutaway view of the arrangement applied to cap for cooling the scalp.
Figure 6:
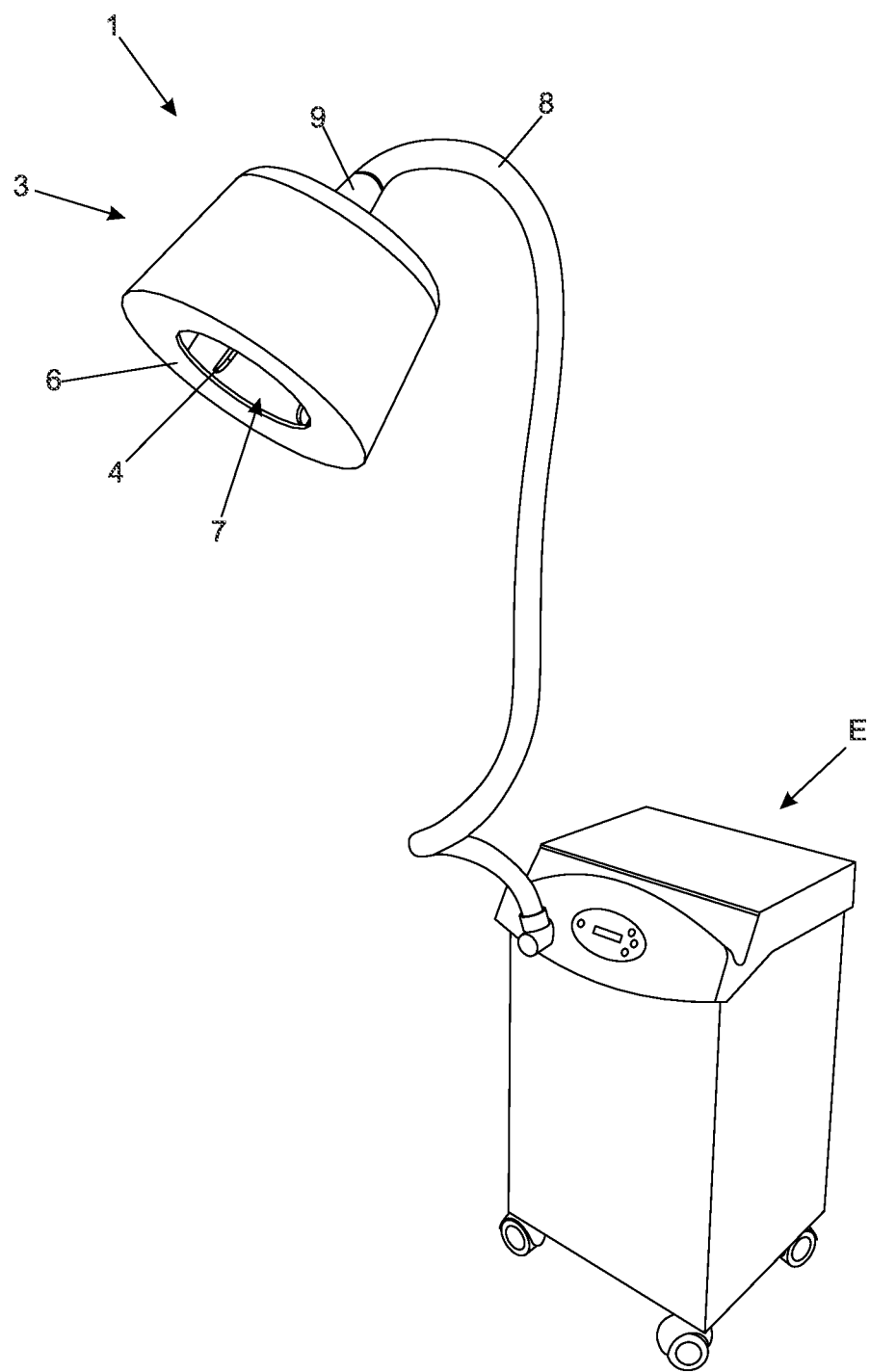
FIG. 6: Perspective view of the arrangement applied to cap for cooling the scalp, showing the assembly of the equipment as a whole.
Figure 7:
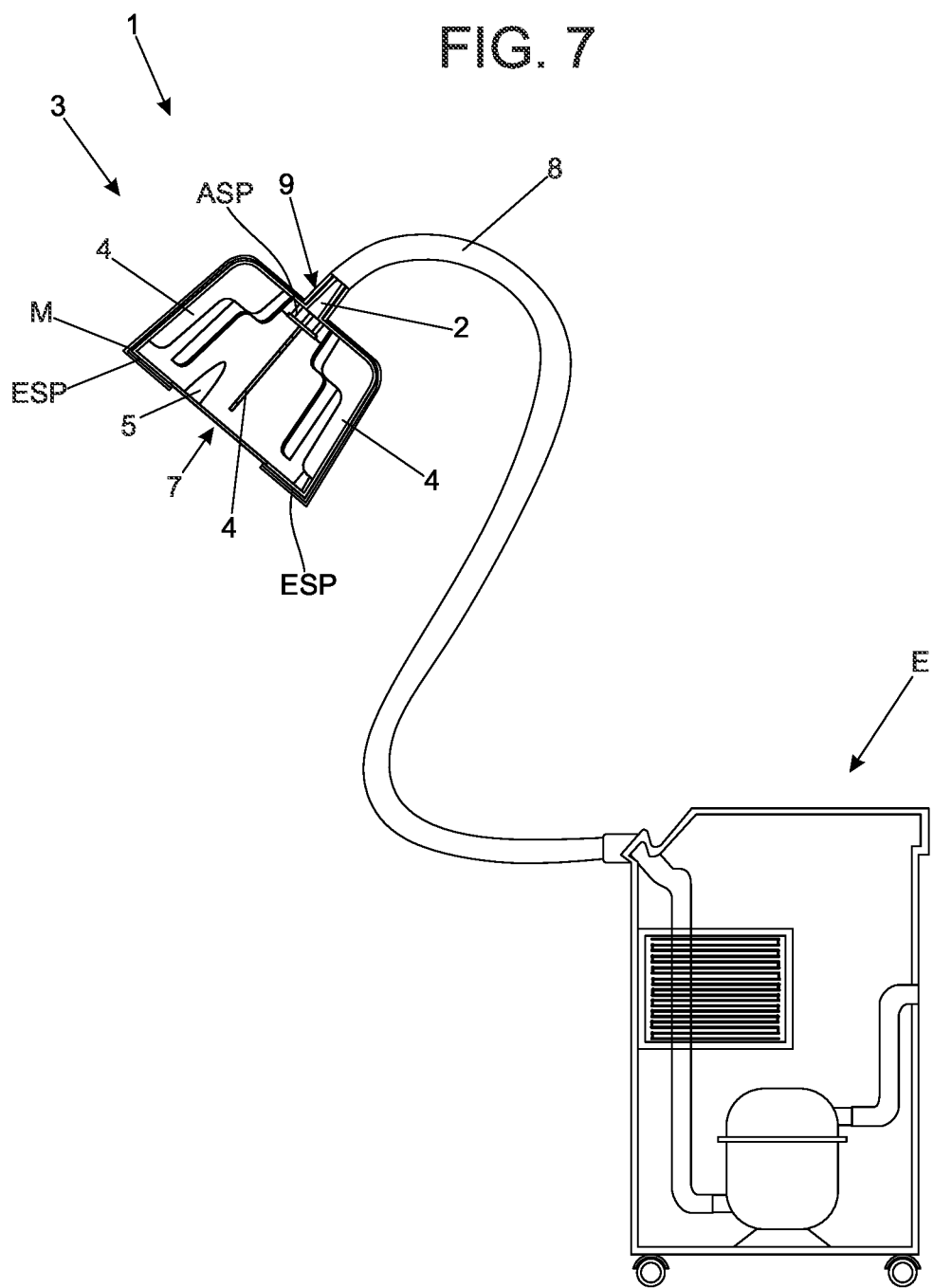
FIG. 7: Side cutaway view of the arrangement applied to cap for cooling the scalp, showing the assembly of the equipment as a whole.
Figure 8:
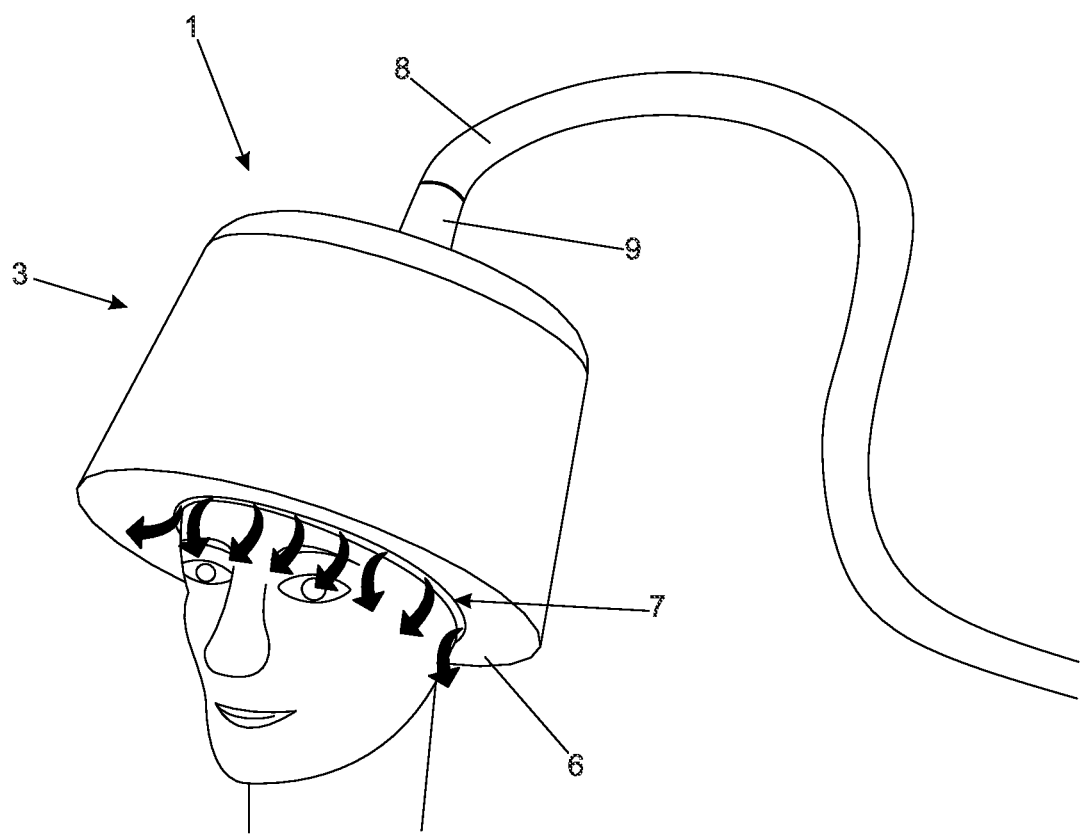
FIG. 8: Perspective view of the arrangement applied to cap for cooling the scalp, showing use.

The ASP as shown in FIGS. 2, 5, and 7, is disposed in the interior of the cap. The distribution member may be below the cylindrical duct (2) to disperse air. The ASP has a bottom surface that may be directly below the opening of the cylindrical duct (2). A perimeter of the bottom surface of the ASP may be bigger than the opening of the cylindrical duct (2). The ASP may have a plurality of edges surrounding a plurality of openings. The plurality of openings perpendicular to the opening of the cylindrical duct (2). The plurality of edges may be adjacent to the plurality of openings and perpendicular to the bottom surface and the opening of the cylindrical duct. The plurality of edges may connect the ASP to the cylindrical duct (2). The plurality of openings may correspond to the interspacing of the of fins (4).

The fins (4), as shown in FIGS. 2, 5, and 7, have a top portion and a bottom portion. The top portion of the fins is disposed proximate to a top portion of the body of the cap and the bottom portion is disposed proximate to a bottom portion of the body of the cap or lower inner portion (I) of the cap (1). The top portion extends inwardly toward the cylindrical duct (2) and terminates at the central opening. The top portion of the finds may be adjacent to the plurality of edges of the ASP. The bottom portion extend inwardly towards the center of the body and terminate before the top portion terminates. The distance between an outer wall (10) of the top portion of the plurality of fins (4) and an inner wall (11) of the top portion of the plurality of fins (4) is greater than a distance between an outer wall (10) of the bottom portion of the plurality of fins (4) and an inner wall (11) of the bottom portion of the plurality of fins (4). The cold air introduced at the central opening is directed between the plurality of fins (4).

The invention claimed is:

1. A cap for evenly cooling the entire scalp to prevent alopecia from chemotherapy, comprising:
   a cylindrical body having a duct disposed in a center of a top portion of the body operably connected to a cold air source for providing cold air to the body and a central opening disposed in a bottom portion of the body configured to receive a top of a patient's head, wherein at least one section of the bottom portion of the body is configured to terminate before reaching the patient's eyes;
   a distribution member connected in communication with the duct for evenly dispersing cold air into the body, wherein the distribution member is disposed in an interior of the top portion of the body; and
   a plurality of fins interspaced within the body between the top portion and the bottom portion of the body, wherein each fin includes a top portion disposed proximate the top portion of the body, a bottom portion disposed proximate the bottom portion of the body, wherein the top portion extends inwardly toward the duct and terminates at the central opening, and wherein cold air introduced at the central opening and directed between the plurality of fins is in contact with the scalp of the patient's head;
   wherein a distance between an outer wall of the top portion of the plurality of fins and an inner wall of the top portion of the plurality of fins is greater than a distance between an outer wall of the bottom portion of the plurality of fins and an inner wall of the bottom portion of the plurality of fins, wherein the outer wall of the top portion of the plurality of fins and the outer wall of the bottom portion of the plurality of fins is contiguous with an inner wall of the body;
   wherein the distribution member and the plurality of fins transform cold air flow from the duct into turbulent and continuous cold air flow within the body for evenly dispersing turbulent and continuous cold air flow towards an entire scalp of the patient's head evenly cooling the entire scalp.

2. The cooling cap of claim 1, wherein the distribution member includes one or more openings for distributing cold air corresponding with interspacing of at least two of the top portions of the plurality of fins.

3. The cooling cap of claim 1, further comprising a thermal foam disposed between an inner wall of the body and an outer wall of the body.

4. The cooling cap of claim 1, wherein the cold air source comprises a cooling unit with a compressor and evaporator.

5. The cooling cap of claim 1, wherein the plurality of fins are perpendicular to an inner wall of the body.

6. The cooling cap of claim 1, further comprising one or more reinforcement ribs disposed in the bottom portion of the body about the central opening, wherein turbulent and continuous cold air flow reaches the reinforcement ribs and wherein a top portion of the reinforcement ribs terminates before the top portion of the plurality of fins.

7. A system for evenly cooling the entire scalp to prevent alopecia from chemotherapy, comprising:
   a cooling unit with a compressor and evaporator, the cooling unit having a discharge for providing cold air;
   a hose having an input end operably attached to the discharge and an opposite discharge end, wherein the hose carries cold air from the cooling unit, through the input end and to the discharge end;
   a cooling cap having a cylindrical body;
   a duct disposed in a top portion of the cap, the duct being operably connected to the discharge end of the hose for introducing cold air from the cooling unit into the cap;
   a central opening disposed in a bottom portion of the cap, the central opening being configured to receive a patient's head, wherein a section of the bottom portion terminates above a patient's eyes;
   a distribution member connected in communication with the duct, the distribution member having a plurality of openings facing an inner wall of the cap for evenly dispersing cold air into the cap, wherein the distribution member is disposed below the duct, wherein the distribution member receives the cold air from the duct and includes a bottom surface disposed beneath a discharge opening of the duct having a perimeter greater than the discharge opening for directing the cold air through the plurality of openings to an entire perimeter of an inner wall of the body, wherein the distribution member is disposed in an interior of the cap, wherein a plurality of edges of the plurality openings connect the distribution member to the duct, wherein the plurality of edges are configured to direct the cold air flow from the duct through the plurality of openings;
   wherein cold air introduced at the plurality of openings is in contact with the scalp of the patient's head; and
   a thermal foam disposed between the inner wall and an outer wall of the cap.

8. The system for cooling the scalp of claim 7, further comprising:
   a plurality of fins interspaced within the cap between the top portion and the bottom portion.

9. The system for cooling the scalp of claim 8, wherein the plurality of fins extend inwardly toward the duct and the central opening.

10. The system for cooling the scalp of claim 8, wherein the plurality of openings distribute cold air corresponding with interspacing of at least two of the plurality of fins.

11. The system for cooling the scalp of claim 8, further comprising:
 a plurality of reinforcement ribs interspaced between the plurality of fins about the bottom portion of the cap.

12. The system for cooling the scalp of claim 7, wherein the distribution member is disposed in the top portion of the cap.

13. The system for cooling the scalp of claim 7, wherein the distribution member and a plurality of fins within the cap transform cold air flow from the duct into turbulent cold air flow within the cap for evenly cooling an entire scalp of the patient's head.

14. A cap for evenly cooling the entire scalp to prevent alopecia from chemotherapy, comprising:
 a cylindrical body having a top portion and an opposite bottom portion configured to be worn on a patient's head;
 a duct disposed in a center of the top portion of the body, the duct configured for operably connecting to a cold air source for providing cold air to the body of the cap;
 a distribution member connected in communication with the duct, the distribution member having a plurality of openings facing an inner wall of the cap, wherein the distribution member receives the cold air from the duct, wherein the distribution member is disposed below the duct in an interior of the top portion of the cylindrical body and includes a bottom surface disposed beneath a discharge opening of the duct having a perimeter greater than the discharge opening for directing the cold air through the plurality of openings to an entire perimeter of an inner wall of the body to cool the entire scalp;
 a central opening disposed in the bottom portion, the central opening being configured to receive the patient's head; and a plurality of fins interspaced within the body between the top portion and the bottom portion, wherein each fin includes a top portion disposed proximate the top portion of the body and the distribution member and a bottom portion disposed proximate the bottom portion of the body, and wherein cold air introduced at the central opening and directed between the plurality of fins is in contact with the scalp of the patient's head;
 wherein the plurality of openings are disposed the top portion of the body of the body downstream of the duct, each of the openings corresponding with a space between each of the plurality of fins, wherein a plurality of edges of the plurality openings connect the distribution member to the duct, wherein the plurality of edges are configured to direct the cold air flow from the duct through the plurality of openings and wherein a first edge of the plurality of edges is adjacent to a first fin of the plurality of fins and a second edge of the plurality of edges is adjacent to a second fin of the plurality of fins;
 a plurality of reinforcement ribs interdisposed about the bottom portion of the body;
 wherein cold air exits the bottom portion of the body through the central opening into ambient air.

15. The cooling cap of claim 14, wherein a distance between an outer wall of the top portion of the plurality of fins and an inner wall of the top portion of the plurality of fins is greater than a distance between an outer wall of the bottom portion of the plurality of fins and an inner wall of the bottom portion of the plurality of fins, wherein the outer wall of the top portion of the plurality of fins and the outer wall of the bottom portion of the fins is adjacent to the inner wall of the body.

16. The cooling cap of claim 15, wherein the duct extends from the distribution member outward from an outer wall of the cap whereby a discharge side of the duct is connected in operable communication within the top portion of the body of the cap.

17. The cooling cap of claim 14, further comprising:
 a thermal foam disposed between the inner wall and an outer wall of the cap.

18. The cooling cap of claim 14, wherein the
 plurality of reinforcement ribs are interdisposed between the plurality of fins.

19. The cooling cap of claim 14, wherein cold air is introduced into the cap at generally between −20° C. and −35° C.

* * * * *